US012575954B2

(12) United States Patent
Wargo

(10) Patent No.: US 12,575,954 B2
(45) Date of Patent: Mar. 17, 2026

(54) DEVICE FOR ALIGNING A USERS PELVIS AND REDUCING LEG LENGTH INEQUITY

(71) Applicant: Evo Fitness LLC, Santa Fe, NM (US)

(72) Inventor: David Wargo, Santa Fe, NM (US)

(73) Assignee: Evo Fitness LLC, Santa Fe, NM (US)

( * ) Notice: Subject to any disclaimer, the term of this patent is extended or adjusted under 35 U.S.C. 154(b) by 191 days.

(21) Appl. No.: 18/436,015

(22) Filed: Feb. 7, 2024

(65) Prior Publication Data

US 2025/0248837 A1 Aug. 7, 2025

(51) Int. Cl.
*A61F 5/01* (2006.01)

(52) U.S. Cl.
CPC .................................. *A61F 5/0193* (2013.01)

(58) Field of Classification Search
CPC .. A61F 5/0193; A61F 5/01; A61F 5/00; A61F 2005/0183; A61F 2005/0181; A61F 5/0102
See application file for complete search history.

(56) References Cited

U.S. PATENT DOCUMENTS

| | | | | |
|---|---|---|---|---|
| 1,635,638 A | * | 7/1927 | Rogers | A61F 5/0193 |
| | | | | 128/882 |
| 2,906,261 A | * | 9/1959 | Craig | A61F 5/0193 |
| | | | | 602/24 |
| 2,963,020 A | * | 12/1960 | Moran | A61F 5/0193 |
| | | | | 602/16 |
| 3,777,747 A | * | 12/1973 | Friedman | A61F 5/0193 |
| | | | | 602/24 |
| 3,892,231 A | * | 7/1975 | Tummillo | A61F 5/0193 |
| | | | | 602/24 |
| 4,392,489 A | | 7/1983 | Wagner, Sr. | |
| 4,574,790 A | * | 3/1986 | Wellershaus | A61F 2/80 |
| | | | | 602/23 |
| 4,576,151 A | * | 3/1986 | Carmichael | A61F 5/0193 |
| | | | | 602/24 |
| 4,805,605 A | | 2/1989 | Glassman | |

(Continued)

FOREIGN PATENT DOCUMENTS

| | | | | |
|---|---|---|---|---|
| NL | 1029502 C2 | * | 1/2007 | A61F 5/0193 |
| SU | 1147393 | | 3/1985 | |
| WO | WO-2007008058 A2 | * | 1/2007 | A61F 5/0193 |

OTHER PUBLICATIONS

"Luna Memory Foam Knee Pillow—Modern Style, Body Positioner, White, Standard Size", Web <https://www.amazon.com/Orthopedic-Pillow-Sciatica-Relief-Pregnancy/dp/B07RYNX8B3/ref=sr_1_7?keywords=Knee%2BWedge&qid=1687016560&sr=8-7&th=1>, retrieved Jun. 19, 2023.

*Primary Examiner* — Tarla R Patel

(57) ABSTRACT

The present invention is a device for aligning a user's pelvis. The device may have a first end with a first end leg cup and a first end strap. A second end may be configured opposite the first end. The second end may have a second end leg cup and second end strap. A bridge may connect the first end and second end. The device may be placed between a user's legs whereby one of the user's legs is configured at least partially within the first end leg cup and the other of the user's legs is configured at least partially within the second leg cup. The user's legs may be secured to the device by the first end strap and second end strap. The user may perform a series of abductions and adductions whereby the device provides resistance to the user which aids in aligning the user's pelvis.

20 Claims, 5 Drawing Sheets

(56)     References Cited

U.S. PATENT DOCUMENTS

| | | | |
|---|---|---|---|
| 5,289,828 A | | 3/1994 | Toth |
| 5,311,366 A | * | 5/1994 | Gerace .................. A61B 90/36 |
| | | | 359/872 |
| D349,541 S | | 8/1994 | Bertolucci et al. |
| 5,362,305 A | | 11/1994 | Varn |
| 5,558,628 A | * | 9/1996 | Bzoch .................. A61F 5/0193 |
| | | | 128/882 |
| 5,681,270 A | | 10/1997 | Klearman et al. |
| 5,895,366 A | | 4/1999 | Bzoch |
| 6,126,624 A | * | 10/2000 | Frauenberger ........ A61F 5/0193 |
| | | | 602/23 |
| 7,223,217 B1 | | 5/2007 | Liao |
| 8,118,764 B2 | * | 2/2012 | Christenhusz ........ A61F 5/0193 |
| | | | 128/870 |
| 8,214,952 B2 | | 7/2012 | Beasley |
| 8,784,279 B2 | | 7/2014 | Cantrell |
| 8,814,760 B2 | | 8/2014 | Hyacinth |
| 9,872,793 B2 | * | 1/2018 | Janning ................ A61F 5/0104 |
| 10,130,836 B2 | | 11/2018 | Madion |
| 11,185,729 B2 | | 11/2021 | Pasterino et al. |
| 11,471,358 B1 | * | 10/2022 | McCullough .......... A63B 23/04 |
| D974,803 S | | 1/2023 | Shi |
| 11,622,899 B2 | | 4/2023 | Fanelli et al. |
| 2006/0217248 A1 | | 9/2006 | Diseati |
| 2009/0229056 A1 | | 9/2009 | Edinger |
| 2012/0214653 A1 | | 8/2012 | Tsou |
| 2021/0077855 A1 | | 3/2021 | Walko |

* cited by examiner

DEVICE FOR ALIGNING A USERS PELVIS AND REDUCING LEG LENGTH INEQUITY

BACKGROUND OF THE INVENTION

The present invention relates to a device that aids in aligning a user's pelvis. Pelvic misalignment can occur due to a number of reasons, including but not limited to unequal leg length ("leg length inequity"), unequal muscle abilities between each leg, low activity, mobility-limiting physical conditions, poor posture, obesity, pregnancy, and childbirth. Pelvic misalignment can cause misalignment in other parts of the body such as the spine and shoulders. Pelvic misalignment can also cause pain in various areas of the body including the head, knees, and feet. Other issues such as digestive issues can even occur due to pelvic misalignment.

Preferred embodiments of the present invention focus on leg length inequity. Leg length inequity can be caused by a number of factors including but not limited to birth defects and trauma. In such cases, leg length inequity can cause pelvic misalignment when one stands on a flat surface with legs of inequal length. In other cases, pre-existing pelvic misalignment may cause leg length inequity.

Common treatments for pelvic misalignment include exercises that focus on the muscles surrounding the pelvis. Sometimes, equipment is used to aid in such exercises in order to provide resistance during the exercises.

SUMMARY OF THE INVENTION

The present invention is a device for aligning a user's pelvis. The device may have a first end with a first end leg cup and a first end strap. A second end may be configured opposite the first end. The second end may have a second end leg cup and second end strap. A bridge may connect the first end and second end. The device may be placed between a user's legs whereby one of the user's legs is configured within or at least partially within the first end leg cup and the other of the user's legs is configured within or at least partially within the second leg cup. The user's legs may be secured to the device by configuring the first end strap and second end strap around the user's legs. The user may perform a series of abductions and adductions whereby the device provides resistance to the user which aids in aligning the user's pelvis.

A length axis may extend from the first end to the second end. A device length may extend from the first end to the second end along the length axis. The device may be a monolithic piece to which the first end strap and second end strap are attached. The device length may only consist of the distance between the first end and second end on the monolithic piece. The device length may be anywhere in the ranges of 3 in-6 in, 4 in-8 in, 6 in-10 in, 8 in-12 in, 10 in-18 in, or any range between or including the values provided.

The device may have a first side and a second side configured opposite the first side. The first side and second side may be separated by a perimeter. A perimeter flange may be configured around the entire perimeter. The perimeter flange may be part of the monolithic piece. The perimeter flange may have a perimeter flange width that may extend from the first side to the second side. The perimeter flange width may be anywhere in the ranges of 0.25 in-1 in, 0.5 in-3 in, 1 in-8 in, or any range between or including the values provided.

Bridge struts may be configured on the bridge. The bridge struts may be part of the monolithic piece. The number of bridge struts may be 2 or more, 3 or more, 4 or more, 5 or more, or any number between or including the values provided. The bridge struts may be connected to the perimeter flange. The bridge struts may be configured perpendicular to the length axis. The bridge struts may extend from the first side to the second side. The bridge struts may be part of the monolithic piece. The bride struts may be arranged in a pattern that extends 5%-15% of the device length, 10%-20% of the device length, 10%-40% of the device length, 15%-50% of the device length, or any range between or including the values provided.

First end struts may extend from the first end leg cup. The first end struts may be part of the monolithic piece. The first end struts may be connected to the perimeter flange. The first end struts may extend from the first side to the second side. The first end struts may be configured at a first end strut angle to the length axis. The number of first end struts may be 2 or more, 3 or more, 4 or more, 5 or more, or any number between or including the values provided. When the first end struts are an even number of first end struts, half of the first end struts may be configured on an opposite side of the length axis than the other half of the first end struts. For example, when the first end struts are 2 first end struts, the 2 first end struts may be configured on opposite sides of the length axis from each other.

Second end struts may extend from the second end leg cup. The second end struts may be part of the monolithic piece. The second end struts may be connected to the perimeter flange. The second end struts may extend from the first side to the second side. The second end struts may be configured at a second end strut angle to the length axis. The number of second end struts may be 2 or more, 3 or more, 4 or more, 5 or more, or any number between or including the values provided. When the second end struts are an even number of second end struts, half of the second end struts may be configured on an opposite side of the length axis than the other half of the second end struts. For example, when the second end struts are 2 second end struts, the 2 second end struts may be configured on opposite sides of the length axis from each other.

The first end strut angle and second end strut angle may both be in the range of 20-60 degrees, inclusive of said values. The first end strut angle and second end strut angle may further be both in the range of 30 degrees-50 degrees, inclusive of said values. The first end strut angle and second end strut angle may be equal. Alternatively, the first end strut angle may be greater than the second end strut angle. Alternatively, the second end strut angle may be greater than the first end strut angle.

Holes may extend from the first side to the second side. The holes may be 1 or more holes, 2 or more holes, 3 or more holes, 4 or more holes, 5 or more holes, or any number between or including the values provided. The holes may have hole diameters. The hole diameters may be 5%-10% of the device length, 7%-15% of the device length, 10%-30% of the device length, or any range between or including the values provided. Each hole may have a different hole diameter than all the other holes. Alternatively, some of the holes may have equal hole diameters. Alternatively, all of the holes may have equal hole diameters.

The device may be made of a material with a Young's Modulus of 7,000 MPa-15,000 MPa, inclusive of said values. Specifically, the monolithic piece of the device may be made of a material with a Young's Modulus of 7,000 MPa-15,000 MPa, inclusive of said values. In preferred embodiments, this material may be a natural wood such as but not limited to pine, oak, cedar, maple, walnut, or a combination of multiple types of natural wood. Natural wood may be used in preferred embodiments due to the Young's Modulus of most natural woods being within the desired range of 7,000 MPa-15,000 MPa. A coating such as but not limited to wood stain, paint, or polyurethane may be applied to the natural wood material of the device.

The material of the device may alternatively be particle board. Particle board is a material made from pieces of natural wood bonded together with a resin or other binder. Particle board may be pressed and/or extruded to achieve desired mechanical properties and/or shape. The advantage of particle board over natural wood is that particle board is often more cost-effective than natural wood. A coating such as but not limited to wood stain, paint, or polyurethane may be applied to the particle board material of the device.

The material of the device may alternatively be concrete. While most grades of concrete have Young's Moduli that are greater than the desired range of 7,000 MPa-15,000 MPa, certain grades of lightweight concrete have Young's Moduli that are below 15,000 MPa. This allows these lightweight grades of concrete to be a suitable material for the device. Lightweight grades of concrete have lower densities than more common grades of concrete. The aggregates used in lightweight grades of concrete are often foam, expanded shale, pumice, or perlites, in contrast to more common grades of concrete that use sand or gravel as aggregates. The concrete material of the device may be coated in another material such as rubber or foam to be more comfortable for the user when the user uses the device.

The Young's Modulus range of 7,000 MPa-15,000 MPa was chosen to provide the optimal amount of resistance to the user when performing abductions and adductions with the device. Highly flexible materials such as less-rigid plastics and rubbers do not provide enough resistance, and therefore the user would not gain any benefits from the abduction and adduction exercises. On the other hand, highly rigid materials provide too much resistance, so the user would not be able to perform any abduction or adduction exercise, and therefore would not gain any benefits from the device.

Alternatively, the device may be made of a material with a Young's Modulus of 2,000 MPa-4,000 MPa, inclusive of said values. Specifically, the monolithic piece of the device may be made of a material with a Young's Modulus of 2,000 MPa-4,000 MPa, inclusive of said values. In preferred embodiments, this material may be a rigid plastic such as but not limited to a high-density polyethylene (HDPE), acrylic, polycarbonate, polyvinyl chloride (PVC), acrylonitrile butadiene styrene (ABS), polystyrene, polyethylene terephthalate (PET), or Delrin®.

The Young's Modulus range of 2,000 MPa-4,000 MPa provides significantly less resistance than that of the Young's Modulus range of 7,000 MPa-15,000 MPa. However, the Young's Modulus range of 2,000 MPa-4,000 MPa still provides enough resistance for the user to gain benefits from the abduction and adduction exercises. Furthermore, the Young's Modulus range of 2,000 MPa-4,000 MPa allows the device to be made of a rigid plastic. Plastic is generally cheaper and easier to manufacture with than the other materials described herein such as wood and concrete. Therefore, manufacturing the device using a rigid plastic would be much more economical for both the manufacturer and the user of the device.

The combination and dimensions of the various holes and struts of the device may also aid in achieving an optimal resistance and elasticity of the entire device. The struts may add to the rigidity of the device whereas the holes may add to the deformability (opposite of rigidity) of the device. The exact placement of struts and holes relative to one another may allow for a higher resistance at the beginning of an abduction/adduction movement and less resistance and the end of an abduction/adduction movement, which may cause the user to engage their muscles in such a way to provide better alignment of their pelvis. Furthermore, the exact placement of struts and holes relative to one another may allow for a greater elasticity of the device immediately after performing an abduction/adduction movement and a lesser elasticity immediately before an abduction/adduction movement, which may allow the user's muscles to rest in such a way to provide better alignment of their pelvis.

The optimal resistance and elasticity of the device achieved by its material(s) of construction of the device as well as the combination, dimensions, and placements of the various holes and struts of the device may also provide better reduction of leg length inequity. Leg length inequity may be reduced by strengthening the muscles surrounding the pelvis. This may result in more equal strength and more equal tension of muscles on either side of the pelvis. This may cause a tilted pelvis to reduce its tilt, thereby reducing the difference in length between the two legs.

The monolithic piece of the device may be widest at the first end leg cup and second end leg cup. The monolithic piece of the device may be narrowest at the bridge. This overall shape may allow the device to easily be grasped and carried by the user. The user may easily grasp the bridge with one hand in order to move the device, thereby making the device highly portable.

The first end leg cup may have a concave curvature relative to the first end strap. The second end leg cup may have a concave curvature relative to the second end strap. The curvatures of the first end leg cup and second end leg cup may allow the device to easily be secured to the user's legs. The curvatures of the first end leg cup and second end leg cup may also provide a more secure connection between the device and the user's legs. A more secure connection between the device and the user's legs may allow the user to engage more of the user's leg muscles when performing abductions and adductions with the device between their legs than they would if they had another object between their legs that was not designed to fit their legs like the first end leg cup and second end leg cup of the device. The engagement of more leg muscles while performing abductions and adductions may help align the user's pelvis more effectively than if the user engaged less of their leg muscles to perform the abductions and adductions. In some embodiments, the device may be available in various sizes wherein the curvatures of the first end leg cup and second end leg cup vary from size-to-size. This allows the device to be used on a large portion of the population.

DETAILED DESCRIPTION

The description provided herein describes example embodiments of the present invention and is not intended to limit the invention to any particular embodiment, use, design, shape, size, feature, component, material, or any other property. Furthermore, the drawings provided herein show example embodiments of the present invention and are not intended to limit the invention to any particular embodiment, use, design, shape, size, feature, component, material, or any other property.

Figure 1:
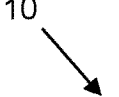
FIG. 1 is a top perspective view of a device for aligning a user's pelvis.

As shown in FIG. 1, a device 10 for aligning a user's pelvis has a first side 12 and a second side 16 configured opposite the first side 12. The device 10 has a first end 20 and a second end 40 configured opposite the first end 20. The device 10 exists as a monolithic piece 18 of material with a first end strap 26 configured at the first end 20 and a second end strap 46 configured at the second end 40. A perimeter 80 is configured around the monolithic piece 18 of the device 10. The perimeter 80 is defined by a perimeter flange 82 that extends from the first side 12 to the second side 16 and is configured around the entire perimeter 80.

The perimeter flange 82 defines a first end leg cup 22 configured at the first end 20 and a second end leg cup 42 configured at the second end 40. The first end leg cup 22 has a concave curvature relative to the first end strap 26. The second end leg cup 42 has a concave curvature relative to the second end strap 46. Two first end struts 30 are connected to the perimeter flange 82 at the first end 20. The first end struts 30 extend from the first side 12 to the second side 16. Two second end struts 50 are connected to the perimeter flange 82 at the second end 40. The second end struts 50 extend from the first side 12 to the second side 16.

A bridge 70 connects the first end 20 to the second end 40. Two bridge struts 74 are connected to the perimeter flange 82 on the bridge 70. The bridge struts 74 extend from the first side 12 to the second side 16. The bridge struts 74 are configured parallel to one another. Three holes 64 are configured on the bridge 70. One of the holes 64 is configured between the two bridge struts 74. The other two holes 64 are configured closer to the first end 20 and the second end 40. The hole 64 configured between the two bridge struts 74 is smaller than the holes 64 configured closer to the first end 20 and second end 40.

Figure 2:
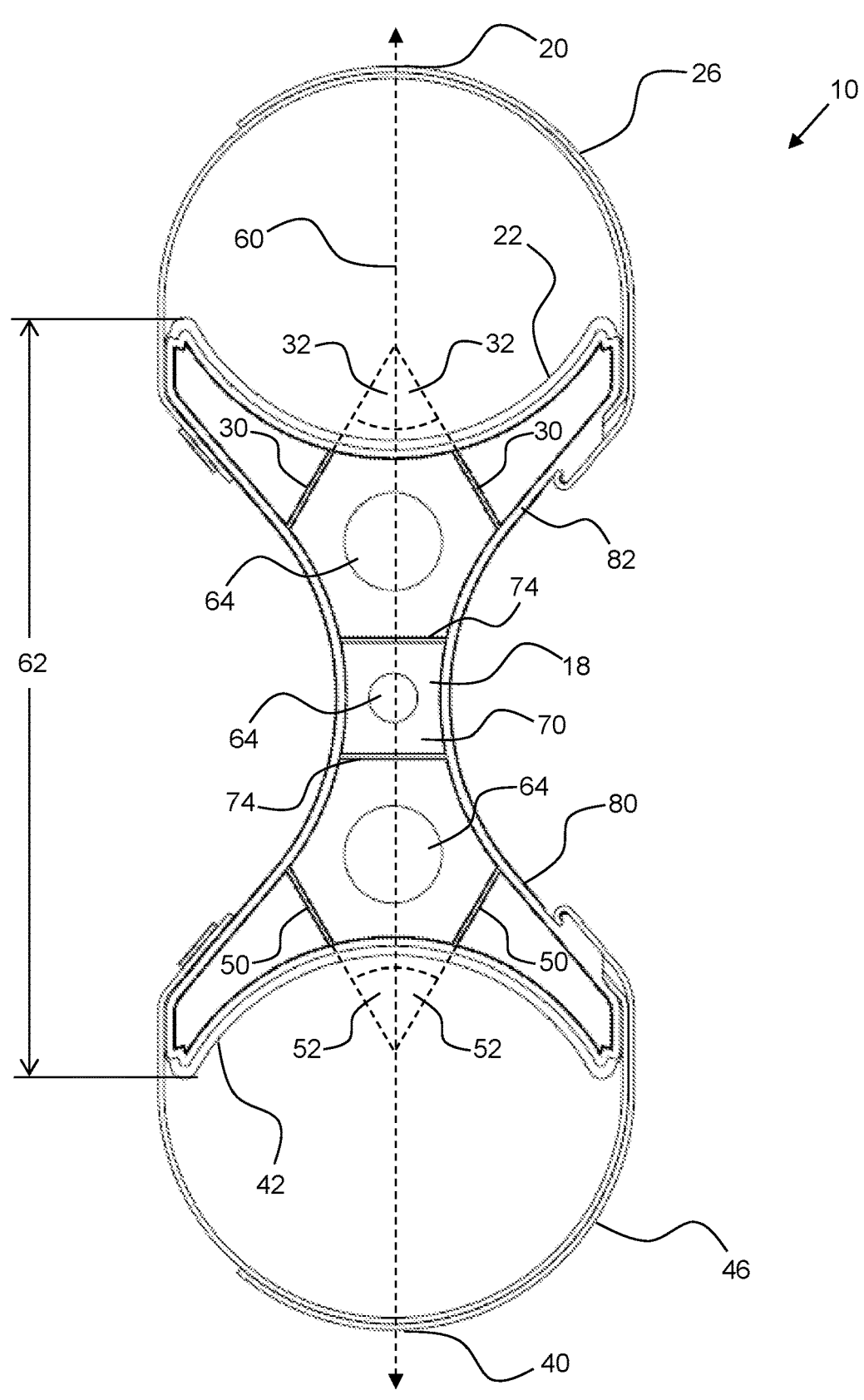
FIG. 2 is a front view of the device of FIG. 1.

As shown in FIG. 2, a length axis 60 extends from the first end 20 to the second end 40. The device 10 has a device length 62 that extends from the first end 20 to the second end 40. The first end strap 26 and second end strap 46 may be much more flexible that the monolithic piece 18, and therefore the device length 62 does not take into account the distance that the first end strap 26 and second end strap 46 extend from the monolithic piece 18.

The bridge struts 74 are configured perpendicular to the length axis 60. The holes 64 are configured in-line with one another along the length axis 60. The first end struts 30 are each configured at a first end strut angle 32 relative to the length axis 60. The second end struts 50 are each configured at a second end strut angle 52 relative to the length axis 60. The first end strut angle 32 of each first end strut 30 may be equal. The second end strut angle 52 of each second end strut 50 may be equal. The first end strut angles 32 may be equal to the second end strut angles 52.

Figure 3:
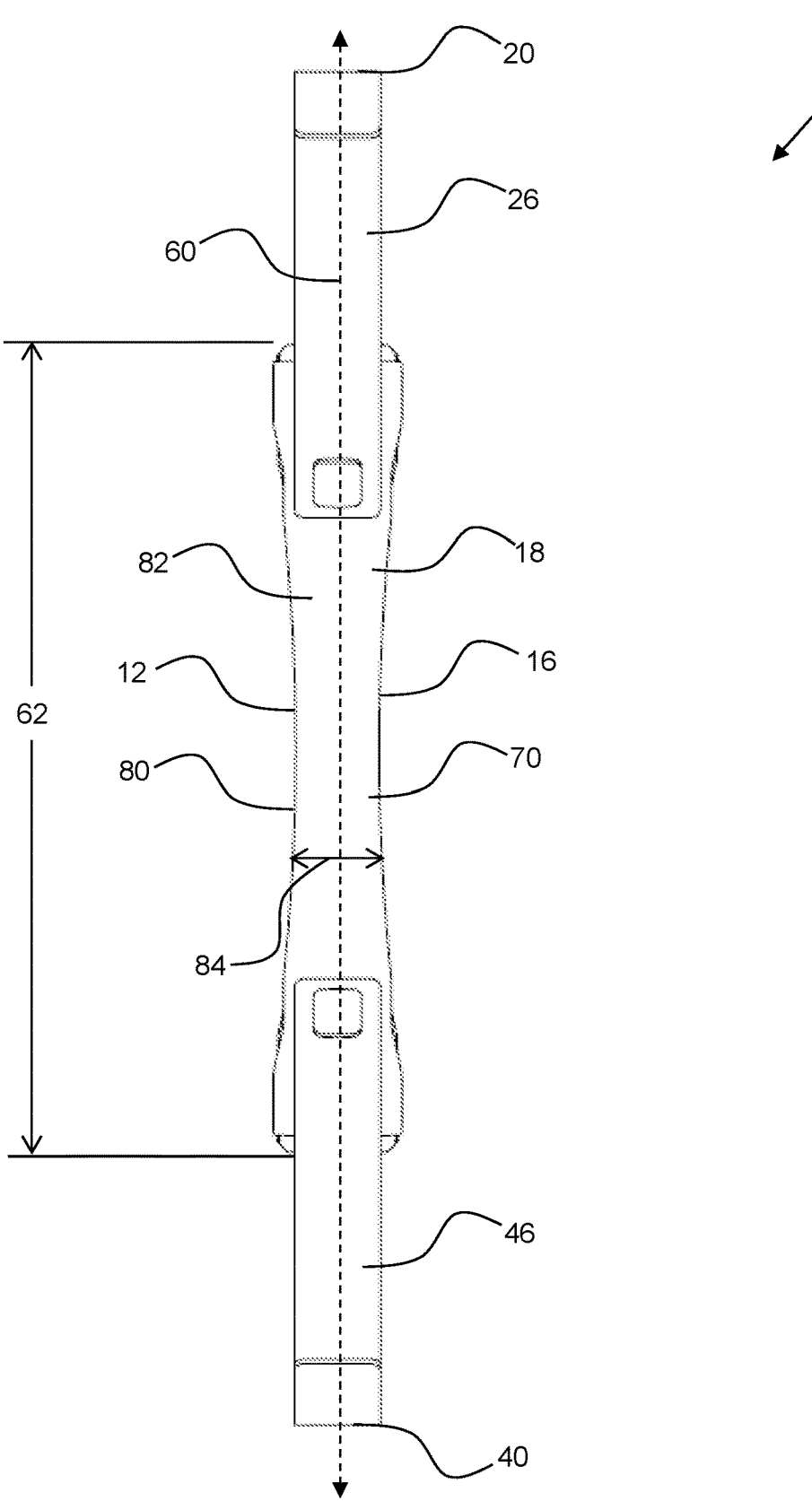
FIG. 3 is a right-side view of the device of FIG. 1.

As shown in FIG. 3, the perimeter flange 82 has a perimeter flange width 84. The perimeter flange width 84 may be different at various locations along the perimeter flange 82. The perimeter flange width 84 may be smaller at the bridge 70 and thicker near the first end 20 and second end 40. The perimeter flange width 84 is measured perpendicular to the length axis 60.

Also as shown in FIG. 3, the perimeter flange 82 extends from the first side 12 to the second side 16. The perimeter flange width 84 may be greater than or equal to corresponding widths of the first end struts, second end struts, and bridge struts. For this reason, the first end struts, second end struts, and bridge struts are not visible in FIG. 3.

Figure 4:
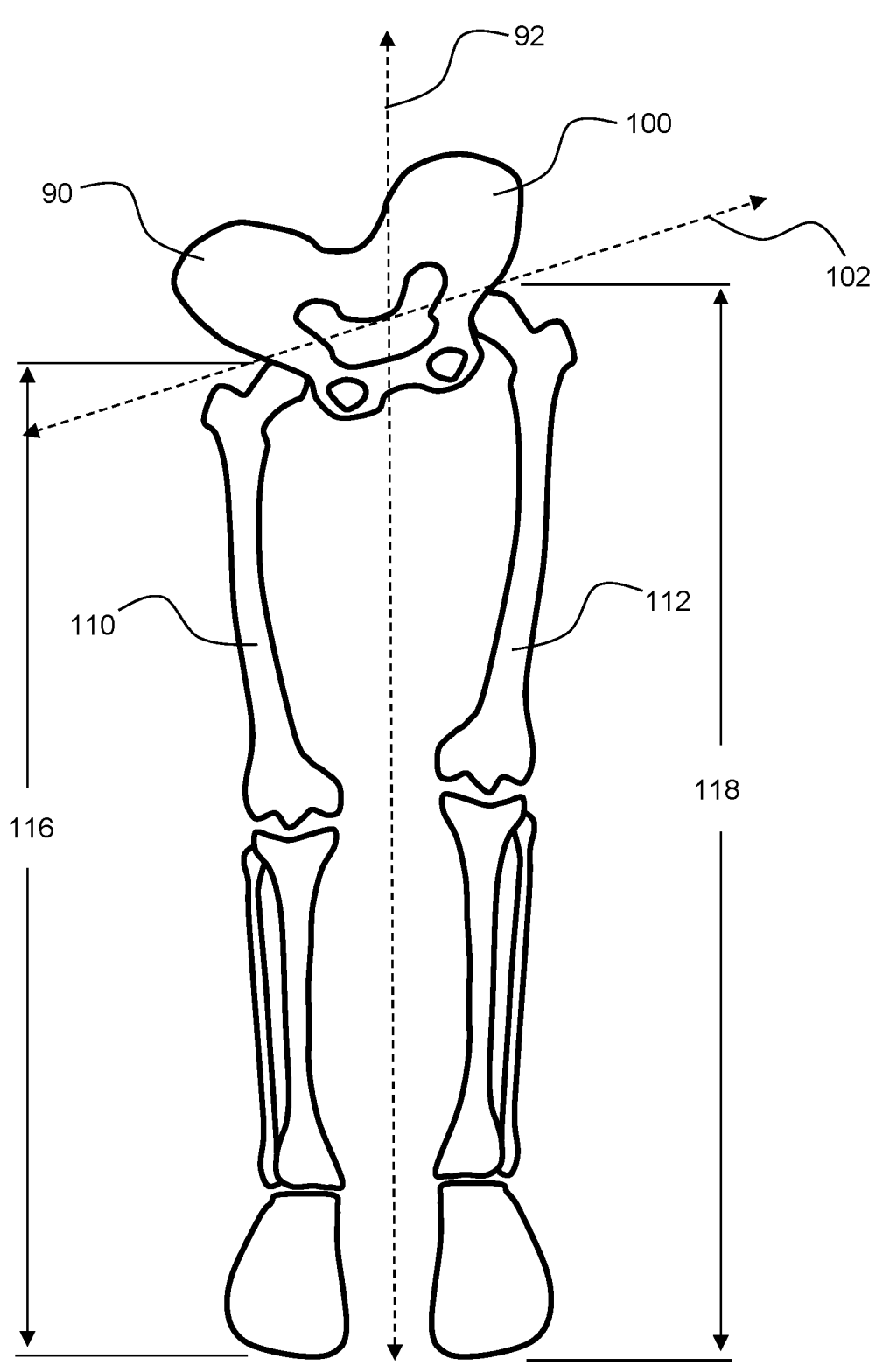
FIG. 4 is a front view of a bottom portion of a skeleton exhibiting leg length inequity.
Figure 5:
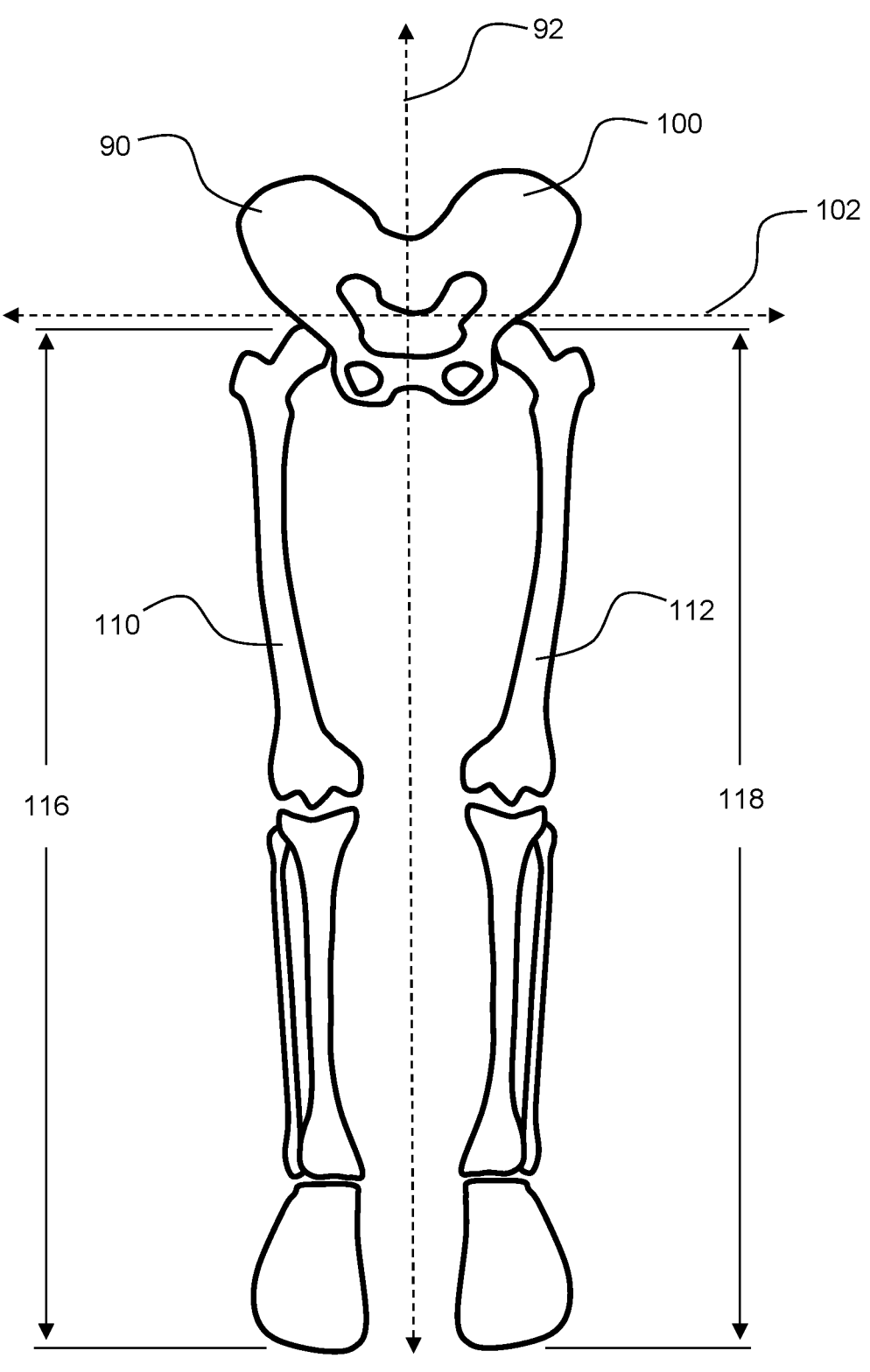
FIG. 5 is the skeleton of FIG. 4 exhibiting no leg length inequity.

As shown in FIGS. 4 and 5, a bottom portion of a skeleton 90 comprises a pelvis 100, a first leg 110 having a first leg length 116, and a second leg 112 having a second leg length 118. A superior-inferior axis 92 is shown that runs directly vertical through the skeleton 90. A pelvic axis 102 is shown that runs from one side of the pelvis 100 to the other side of the pelvis 100 through a center of the pelvis 100. As shown in FIG. 5, the pelvic axis 102 is configured perpendicular to the superior-inferior axis 92. In FIG. 5 the pelvis 90 is aligned. The first leg length 116 equals the second leg length 118. No leg length inequity is exhibited by the skeleton 90.

As shown in FIG. 4, the pelvis 100 is tilted whereby the pelvic axis 102 is not perpendicular to the superior-inferior axis 92. The pelvis 90 is not aligned. The first leg length 116 is smaller than the second leg length 118. Leg length inequity is exhibited by the skeleton 90.

In order to be considered aligned, the pelvis 90 may have a pelvic axis 102 that is within 1 degree of perpendicular with the superior-inferior axis 92. In order to be considered equal (whereby no leg length equity is exhibited), the first leg length 116 and second leg length 118 may be within 3% of each other.

FIG. 4 shows an example skeleton before the device of the present invention is used. FIG. 5 shows the same skeleton after the device of the present invention is used. As shown in FIGS. 4 and 5, use of the device of the present invention to perform abductions and adductions may cause the pelvis to reduce its tilt, and thereby reduce leg length inequity.

What is claimed is:

1. A device comprising:
   a first end comprising:
      a first end leg cup;
      a first end strap;
   a second end comprising:
      a second end leg cup;
      a second end strap;
   a length axis extending from the first end to the second end;
   a bridge connecting the first end and second end;
   a first side;
   a second side configured opposite the first side;
   a perimeter comprising a perimeter flange;
   bridge struts configured on the bridge,
      wherein the bridge struts are connected to the perimeter flange,
      wherein the bridge struts are configured perpendicular to the length axis,
      wherein the bridge struts extend from the first side to the second side;
   first end struts extending from the first end leg cup,
      wherein the first end struts are connected to the perimeter flange,
      wherein the first end struts are configured at a first end strut angle to the length axis,
      wherein the first end struts extend from the first side to the second side;
   second end struts extending from the first end leg cup,
      wherein the second end struts are connected to the perimeter flange,
      wherein the second end struts are configured at a second end strut angle to the length axis,
      wherein the second end struts extend from the first side to the second side; and

holes extending from the first side to the second side,
wherein the device is placed between a user's legs
whereby one of the user's legs is configured at least
partially within the first end leg cup and the other of the
user's legs is configured at least partially within the
second end leg cup,
wherein the first end strap and second end strap are
configured around the user's legs to secure the device
to the user's legs,
wherein the user performs a series of abductions and
adductions, whereby the device provides resistance
when a user performs the series of abductions and
adductions,
whereby the resistance of the device aids in aligning the
user's pelvis.
2. The device of claim 1, wherein first end strut angle and
second end strut angle are both in the range of 20 degrees-60
degrees.
3. The device of claim 2, wherein the first end strut angle
and second end strut angle are both in the range of 30
degrees-50 degrees.
4. The device of claim 2, wherein the first end strut angle
and second end strut angle are equal.
5. The device of claim 1, wherein the bridge struts are 2
or more bridge struts.
6. The device of claim 5, wherein the bridge struts are 3
or more bridge struts.
7. The device of claim 5, wherein the bridge struts are 4
or more bridge struts.
8. The device of claim 1, further comprising a device
length extending from the first end to the second end,
wherein the bridge struts are arranged in a pattern that
extends 10%-40% of the device length.

9. The device of claim 8, wherein the bridge struts are
configured 10%-20% of the device length from one another.
10. The device of claim 1, wherein the holes are 2 or more
holes.
11. The device of claim 10, wherein the holes are 3 or
more holes.
12. The device of claim 1, wherein the holes have hole
diameters that are 5%-10% of the device length.
13. The device of claim 1, wherein the holes are config-
ured 10%-30% of the device length from one another.
14. The device of claim 1, wherein the first end struts are
two first end struts,
wherein the two first end struts are configured on opposite
sides of the length axis,
wherein the second end struts are two second end struts,
wherein the two second end struts are configured on
opposite sides of the length axis.
15. The device of claim 1, wherein the perimeter flange
has a perimeter flange width, and wherein the perimeter
flange width is 1 in-8 in thick.
16. The device of claim 1, wherein the device is made of
a material with a Young's Modulus of 7,000 MPa-15,000
MPa.
17. The device of claim 16, wherein the device is made of
a natural wood.
18. The device of claim 1, wherein the device is made of
a material with a Young's Modulus of 2,000 MPa-4,000
MPa.
19. The device of claim 18, wherein the device is made of
a rigid plastic.
20. The device of claim 1, wherein the resistance of the
device aids in reducing leg length inequity.

* * * * *